United States Patent
Iera et al.

(10) Patent No.: US 6,960,686 B2
(45) Date of Patent: Nov. 1, 2005

(54) PREPARATION AND PURIFICATION OF ANTIVIRAL DISULFONIC ACID DISODIUM SALT

(75) Inventors: Silvio Iera, Montreal (CA); Christopher A. Demerson, Kirkland (CA); Jacqueline F. Lunetta, Pierrefonds (CA); Maria Papamichelakis, Montreal (CA); Michael F. MacEwan, Monroe, NY (US); Wayne G. McMahon, Harriman, NY (US); John R. Potoski, West Nyack, NY (US); Arthur G. Mohan, Somerville, NJ (US); Antonia Nikitenko, Tarrytown, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/946,842

(22) Filed: Sep. 22, 2004

(65) Prior Publication Data

US 2005/0038026 A1 Feb. 17, 2005

Related U.S. Application Data

(62) Division of application No. 10/066,356, filed on Jan. 31, 2002, now Pat. No. 6,806,366.
(60) Provisional application No. 60/266,124, filed on Feb. 2, 2001.

(51) Int. Cl.[7] .................... C07C 303/00; A61K 31/18
(52) U.S. Cl. .......................................... 564/86; 564/87
(58) Field of Search ...................... 564/87, 86

(56) References Cited

U.S. PATENT DOCUMENTS

| | | |
|---|---|---|
| 5,359,131 A | 10/1994 | Curtis et al. |
| 5,429,767 A | 7/1995 | Zelger |
| 5,852,015 A | 12/1998 | Gluzman et al. |

FOREIGN PATENT DOCUMENTS

| | | |
|---|---|---|
| EP | 0795549 | 9/1997 |

OTHER PUBLICATIONS

Ellestad et al., "Novel and specific respiratory syncytial virus inhibitors that target virus fusion," J. Med. Chem. 41:2671–2675 (1998).

Huang–Minlon, "The Reaction of Hydrazine Hydrate on Nitro–Compounds and a New Route to Synthetic Oestrogens," J. Am. Chem. Soc. 70(8):2802–2805 (1948).

Nikitenko et al., "The Discovery of RFI–641 as a Potent and Selective Inhibitor of the Respiratory Syncytial Virus," Bioorganic & Medicinal Chemistry Letters, 11(8):1041–1044 (Apr. 23, 2001).

Razinkov et al., "RFI–641 inhibits entry of respiratory syncytial virus via interactions with fusion protein," Chemistry & Biology 8(7):645–659 (2001).

*Primary Examiner*—Richard L. Raymond
*Assistant Examiner*—Kahsay Habte
(74) *Attorney, Agent, or Firm*—John W. Hogan, Jr.; Anne M. Rosenblum

(57) ABSTRACT

The present invention provides a new process and intermediates for the production of antiviral compound 4',4-bis-{4,6-bis-[3-(bis-carbamoyl-methyl-1-sulfamoyl)-phenylamino]-[1,3,5]triazin-2-ylamino}-biphenyl-2,2'-disulfonic acid and its pharmaceutically acceptable salts.

4 Claims, No Drawings

PREPARATION AND PURIFICATION OF ANTIVIRAL DISULFONIC ACID DISODIUM SALT

This application is a divisional application of Nonprovisisonal Application Ser. No. 10/066,356, filed Jan. 31, 2002 now U.S. Pat. No. 6,806,366, which is claims the benefit under 35 U.S.C. § 119(e) of U.S. Provisional Application No. 60/266,124, filed Feb. 2, 2001, abandoned, the entire discloser of which is hereby incorporated by reference.

This invention concerns methods for the preparation, purification and isolation of antiviral disulfonic acid, disodium salt, particularly 4',4-bis-{4,6-bis-[3-(bis-carbamoyl-methyl-1-sulfamoyl)-phenylamino]-[1,3,5]triazin-2-ylamino}-biphenyl-2,2'-disulfonic acid, as well as intermediates useful for its synthesis.

BACKGROUND OF THE INVENTION

Ellestad et al, J. Med. Chem. 41, 2671 (1998) and U.S. Pat. No. 5,852,015 describe a method for preparation and purification of 4',4-bis-{4,6-bis-[3-(bis-carbamoyl-methyl-1-sulfamoyl)-phenylamino]-[1,3,5]triazin-2-ylamino}-biphenyl-2,2'-disulfonic acid. The intermediates of this disclosed process, when used in subsequent steps lead to an approximately 70% product purity by HPLC, which requires extensive reverse phase chromatographies, followed by lyophilization to remove residual solvents. The process of Ellestad et al. may be summarized in the following Scheme I.

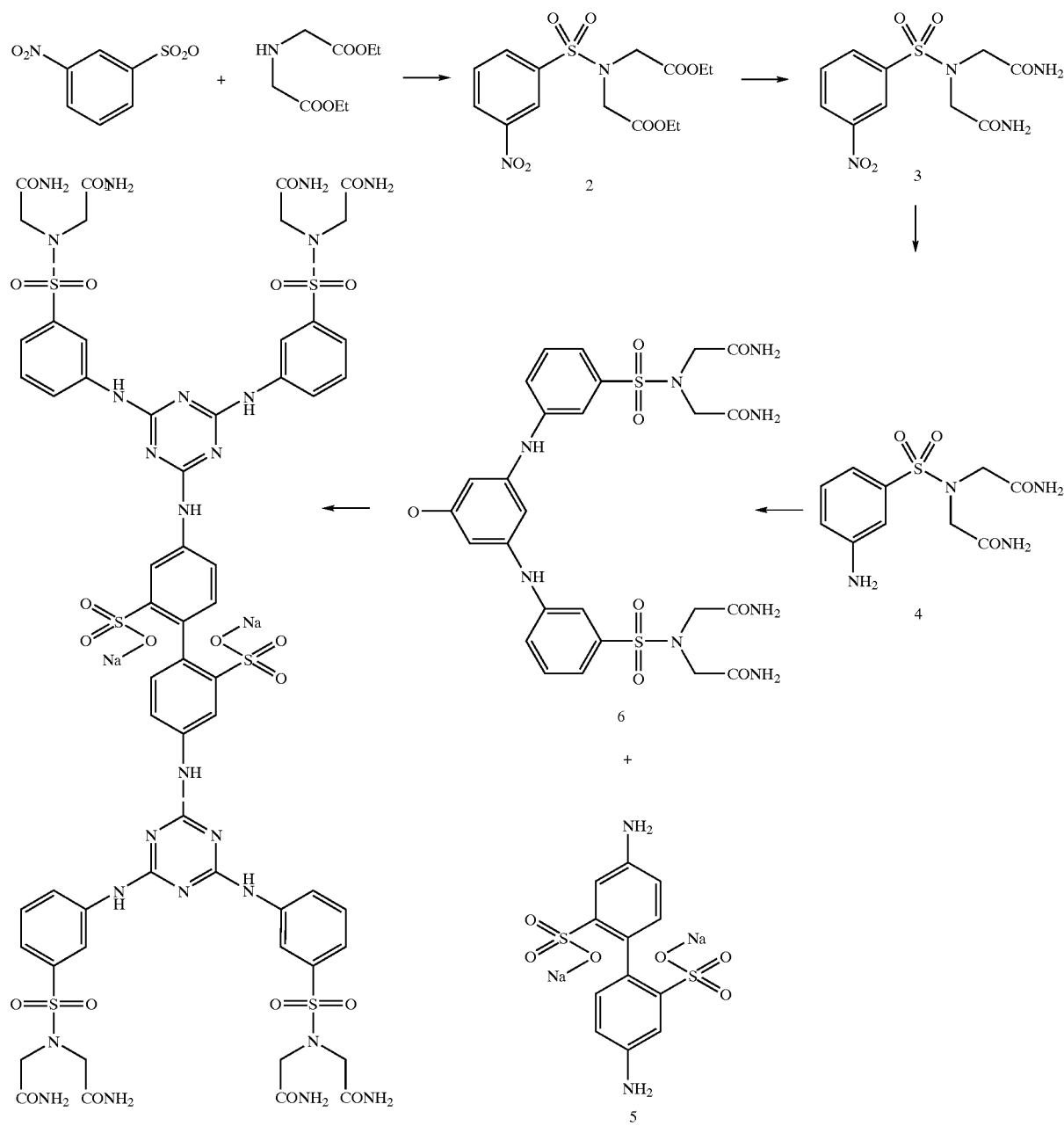

Scheme I

The use of pure intermediates leads to a higher purity crude 4',4-bis-{4,6-bis-[3-(bis-carbamoyl-methyl-1-sulfamoyl)-phenylamino]-[1,3,5]triazin-2-ylamino}-biphenyl-2,2'-disulfonic acid. Formation of impurities that require chromatography to remove can be further reduced by performing the last reaction step at a temperature range of 60–75° C. A purity of better than 80% can be obtained. It is desirable to have a process by which even greater purity can be achieved.

SUMMARY OF THE INVENTION

This invention provides processes by which a higher purity product can now be achieved with better than 97% purity by precipitation/crystallization from a volume of acetonitrile:water, without the use of tedious or costly chromatographies and lyophilizations. Preferably the volume of acetonitrile:water comprises a mixture ratio of from about 0.75:2 to about 1.5:2, more preferably from about 0.8:2 to about 1.2:2, most preferably about 1:2.

This invention provides a process for the production of 2-[Carbamoylmethyl-(3-nitro-benzenesulfonyl)-amino]acetamide, the method comprising reacting 2-(3-Nitro-benzenesulfonylamino)-acetamide with $ClCH_2CONH_2$ in the presence of an aprotic solvent, such as N,N-Dimethylformamide (DMF), and a base. Commercially available bases, such as N,N,N',N'-tetramethyl-1,8-naphthalenediamine, sodium carbonate, potassium carbonate or sodium bicarbonate, may be utilized. The pH of useful aqueous reaction medium is preferably maintained as either neutral or slightly acidic, preferably a pH range of from about 6 to about 7, more preferably from about 6.5. In non-aqueous media a stoichiometric excess of base may be utilized. Other useful bases include, but are not limited to, sodium hydride, potassium hydride and KOH in mixtures of alcohol(s) and water.

This procedure for the preparation of the intermediate 2-[Carbamoylmethyl-(3-nitro-benzenesulfonyl)-amino]acetamide may be further characterized as comprising an initial step of preparing 2-(3-Nitro-benzenesulfonylamino)-acetamide by reacting 3-Nitro-benzenesulfonyl chloride with aminoglycine hydrochloride or its free base in the presence of a base. The pH of the reaction medium can be created using commercially available bases, such as sodium carbonate or sodium bicarbonate. This step is preferably carried out at a pH of from about 5 to about 8, more preferably from about 6.5 to about 7.

This invention further provides a process for the synthesis of 4',4-bis-{4,6-bis-[3-(bis-carbamoyl-methyl-1-sulfamoyl)-phenylamino]-[1,3,5]triazin-2-ylamino}-biphenyl-2,2'-disulfonic acid, the process comprising the steps of:

a) reacting 2-(3-Nitro-benzenesulfonylamino)-acetamide with $ClCH_2CONH_2$ in the presence of N,N-Dimethylformamide and a base to provide 2-[Carbamoylmethyl-(3-nitro-benzenesulfonyl)-amino]acetamide;

b) treating the 2-[Carbamoylmethyl-(3-nitro-benzenesulfonyl)-amino]-acetamide product of step a) with a reducing agent to provide 2-[(3-Amino-benzenesulfonyl)-carbamoylmethyl-amino]acetamide;

c) treating the 2-[(3-Amino-benzenesulfonyl)-carbamoylmethyl-amino-acetamide product of step b) with cyanuric chloride, 2,4,6-trichloro-1,3,5-triazine, to give 2-[(4-{4-[4-(Bis-carbamoylmethyl-sulfamoyl)-benzyl]-6-chloro-[1,3,5]triazin-2-ylmethyl}-benzenesulfonyl)-carbamoylmethyl-amino]acetamide; and d) reacting the 2-[(4-{4-[4-(Bis-carbamoylmethyl-sulfamoyl)-benzyl]-6-chloro-[1,3,5]triazin-2-ylmethyl}-benzenesulfonyl)-carbamoylmethyl-amino]acetamide product of step c) with the disodium salt of 4,4'-diamino-2,2'-biphenyldisulfonic acid.

The resulting product of this process may be converted to pharmaceutically acceptable salts thereof by methods known in the art.

More specifically, the process described herein differs from the processes described in J. Med. Chem. 41, 2671 (1998) and in U.S. Pat. No. 5,852,015, outlined in Scheme I, above, in the preparation of intermediate 3, N,N'-bisacetamido-3-nitrobenzenesulfonamide (see examples for detailed procedures).

Scheme II

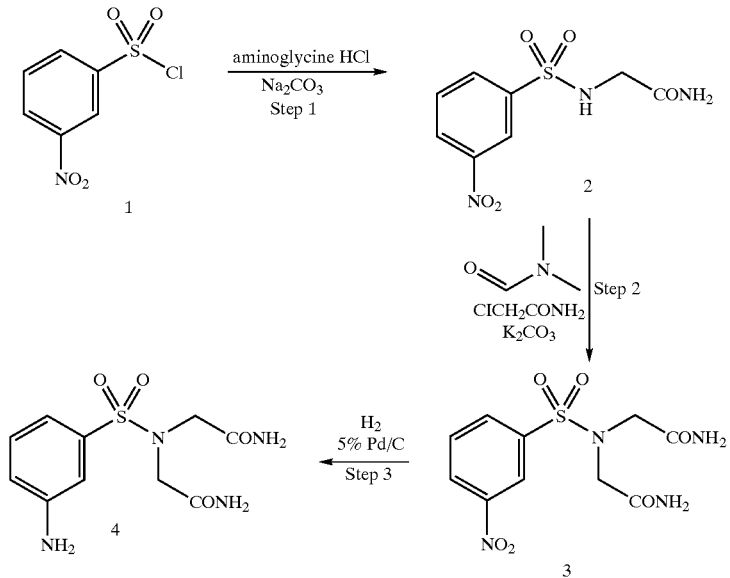

As depicted in Scheme II, m-Nitrobenzenesulfonyl chloride can be reacted with commercially available aminoglycine hydrochloride or its free base in aqueous alkali medium to afford intermediate 2, 2-(3-Nitro-benzenesulfonylamino)-acetamide, in high yields. Commercially available and art recognized bases may be used to prepare the alkali medium. Preferred bases are sodium carbonate, sodium bicarbonate, potassium hydroxide, potassium carbonate, potassium bicarbonate, sodium hydroxide, and triethylamine. Intermediate 2 can be further substituted by condensation with an α-haloacetamide in aqueous alkali medium to give intermediate 3, 2-[carbamoylmethyl-(3-nitro-benzenesulfonyl)-amino]-acetamide. Chloroacetamide is preferred due to large scale availability and cost. Preferred bases are the alkali carbonates, such as potassium carbonate or sodium carbonate.

While the remainder of the steps in the process are the same as in Scheme I, the quality of the subsequent intermediates and crude 4',4-bis-{4,6-bis-[3-(bis-carbamoyl-methyl-1-sulfamoyl)-phenylamino]-[1,3,5]triazin-2-ylamino}-biphenyl-2,2'-disulfonic acid, disodium salt have been much improved, permitting the use of simple isolation and purification techniques.

Nitro intermediate 3 is subjected to reduction conditions to afford the amino intermediate 4, 2-[(3-Amino-benzenesulfonyl)-carbamoylmethyl-amino]acetamide. This reduction may be accomplished using reducing agents known in the art, including iron/acetic acid, iron/HCl, granular tin/HCl, $SnCl_2$/HCl, or $H_2S$ in aqueous or alcoholic ammonia. The preferred method is catalytic reduction, more specifically using palladium on carbon catalyst in DMF. Use of acid in the reduction has been eliminated, thus simplifying isolation. Without a recrystallization the quality of this intermediate has been raised to approximately 99% by the present procedure, further described in Example 3.

Scheme III

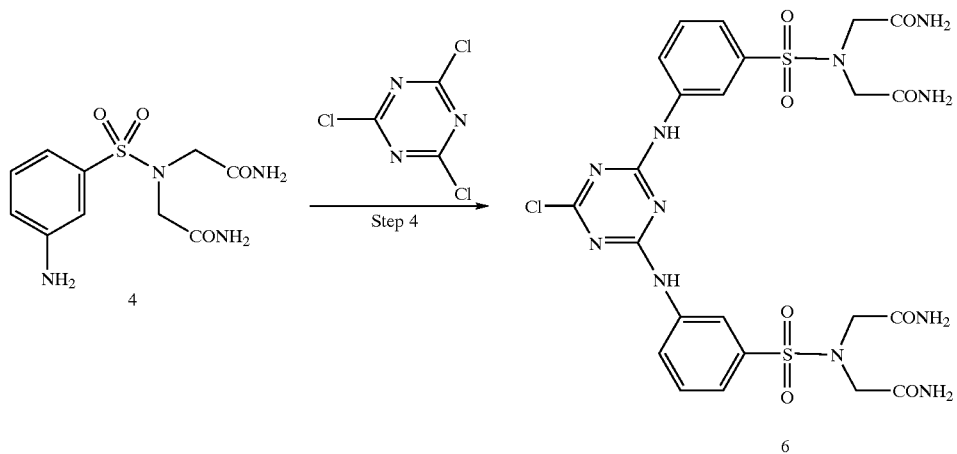

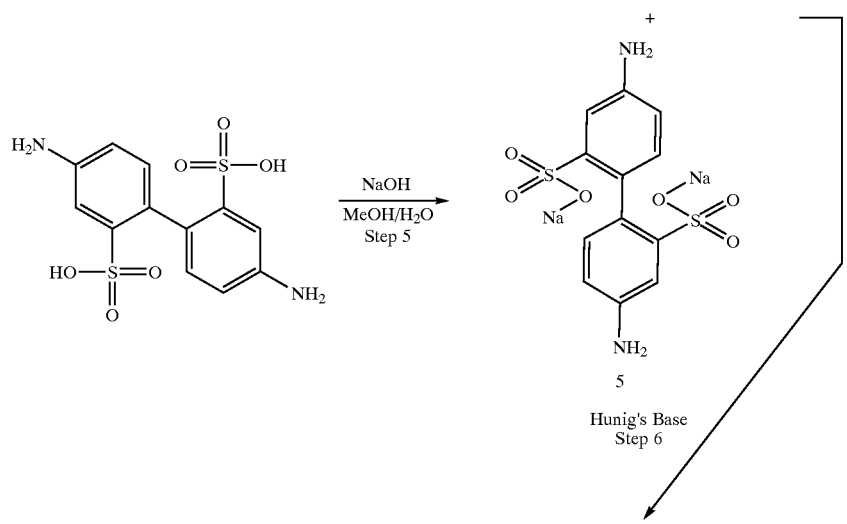

Hunig's Base
Step 6

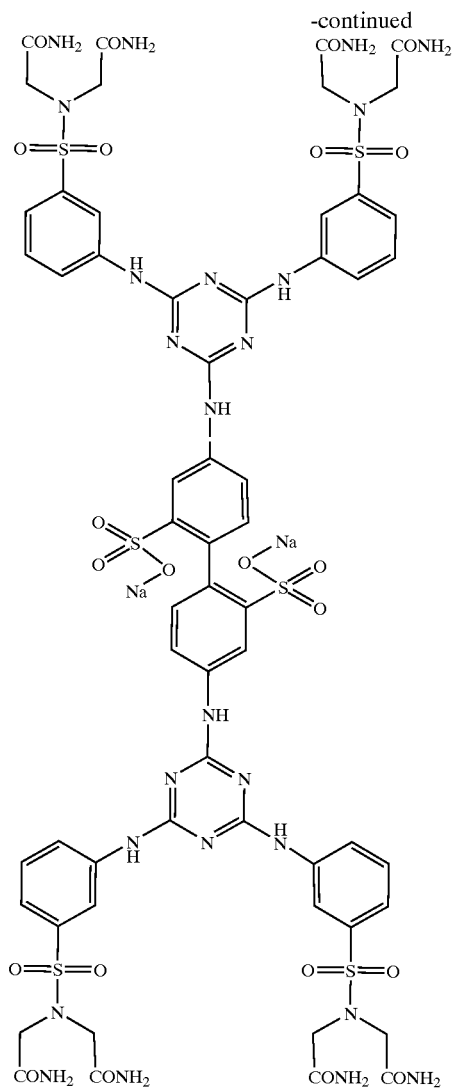

-continued

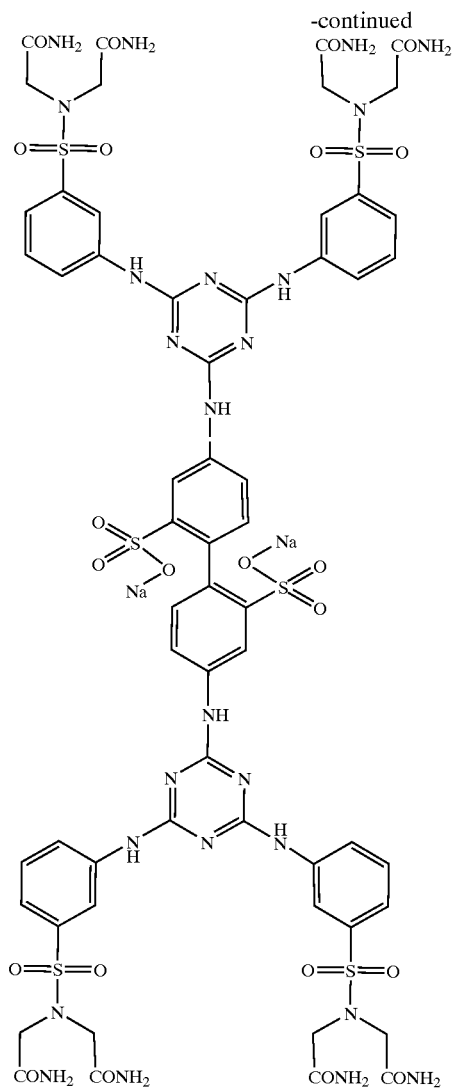

The condensation of intermediate 4 with cyanuric chloride to give intermediate 6, 2-[(4-{4-[4-(Bis-carbamoylmethyl-sulfamoyl)-benzyl]-6-chloro-[1,3,5] triazin-2-ylmethyl}-benzenesulfonyl)-carbamoyimethyl-amino]acetamide, as described in J. Med. Chem. 41, 2671 (1998) and in U.S. Pat. No. 5,852,015, requires a reaction vessel or container temperature of 100–120° C. and the pH to be kept at 6.5–7.2 by the use of a phosphate buffer. It has been found that this condensation can be done without consideration of pH and the use of buffers. Also, the reaction may be carried out at a much lower temperatures in 1-methyl-2-pyrrolidinone and in the presence of sodium carbonate. This reaction can be completed for example at a temperature of from about 10° C. to about 90° C., more preferably at a temperature of from about 10° C. to about 40° C., most preferably from about 20° C. to about 25° C. The isolated penultimate intermediate 6 optionally can be further purified by recrystallization from 1-methyl-2-pyrrolidinone-water mixture.

This invention further comprises a process for the purification of intermediate 6, 2-[(4-{4-[4-(Bis-carbamoylmethyl-sulfamoyl)-benzyl]-6-chloro-[1,3,5] triazin-2-ylmethyl}-benzenesulfonyl)-carbamoylmethyl-amino]acetamide, the process comprising dissolving an amount of intermediate 6 in a volume of water and 1-methyl-2-pyrrolidinone, followed by addition of excess water to precipitate a more purified amount of intermediate 6. Preferably, the ratio of water:1-methyl-2-pyrrolidinone into which the amount of intermediate 6 is dissolved is from about 1:1. Precipitation of the desired product can then be completed by adding additional water to create a water:1-methyl-2-pyrrolidinone ratio of up to about 6:1 (wt:wt), more preferably from 3:1 to about 5:1 (wt:wt), more preferably about 4:1 (wt:wt).

The final step requires a condensation of intermediate 6 with the disodium salt of 4,4'-diamino-2,2'-biphenyldisulfonic acid 5 in the presence of a base, such as Hunig's base (diisopropylethylamine) or another trialkylamine base, such as tributylamine or triethylamine. J. Med. Chem. 41, 2671 (1998) and U.S. Pat. No. 5,852,015 teaches that this reaction requires a temperature of over 100° C. to displace the chlorine of intermediate 6. While this reaction may be conducted at temperatures of up to about 120° C., it has been found that this reaction can best be done at a lower temperature. By performing this reaction at a lower temperature impurities that hinder purification are minimized and 4',4-Bis-{4,6-bis-[3-(bis-carbamoyl-methyl-1-sulfamoyl)-phenylamino]-[1,3,5]triazin-2-yl-amino}- biphenyl-2,2'-disulfonic acid, disodium salt can be obtained without the use of chromatographies and lyophilizations. This step may be conducted at a temperature of from about 15° C. or higher, preferably about 20° C. or higher and most preferably at a temperature of from about 50° C. or higher, up to about 100° C., more preferably up to 90° C., and even more preferably up to a temperature of about 80° C. The most preferred temperature range is from about 60° C. to 75° C. The preferred solvent is dimethyl sulfoxide (DMSO). 4',4-Bis-{4,6-bis-[3-(bis-carbamoyl-methyl-1-sulfamoyl)-phenylamino]-[1,3,5]-triazin-2-ylamino}-biphenyl-2,2'-disulfonic acid, disodium salt produced by this process is typically of 80–85% purity by HPLC. It can be further purified by precipitation/crystallization from acetonitrile-water (1:2 v/v) and filtration at an elevated temperature, such as from about 30° C. to about 60° C., preferably at a temperature of about 50° C. In this process the compound can be dissolved in a volume of acetonitrile/water of about 1:2 (v:v), followed by addition of additional acetonitrile until crystallization of the compound is achieved, preferably at a final concentration of acetonitrile:water of about 2:1.

EXAMPLE 1

Preparation of N-Acetamido-3-nitrobenzenesulfonamide

Charge 3-nitrobenzenesulfonyl chloride (1000 g, 4.52 mol) followed by potable water (2250 g) to a 4-necked 12 L round-bottomed flask equipped with a mechanical stirrer, a temperature probe, a dropping funnel and an inlet for a pH probe. To the resulting amber colored slurry add glycinamide HCl (600 g, 5.42 mol). Stir the resulting slurry at 22° C. for 0.5 hour. To the slurry add, via the dropping funnel, $Na_2CO_3$ solution (prepared from 525 g $Na_2CO_3$, 10 mol, and 1850 g potable water), while maintaining a pH between 6.0 and 6.9. The pH prior to any base is 3.0. Once a pH of ~6.5 is reached, the drop rate is set so that a pH of 6.5 to 6.9 is maintained. The pH is monitored continuously with the pH probe throughout the addition. Fast stirring in the reaction flask assures that the droplets of incoming base (pH=11) mix well. The addition requires a period of 2 hours. Rinse the dropping funnel with potable water (50 g). Stir at 22° C. for 20 h. Check for reaction completion by quantitative TLC or HPLC. If not complete add more glycinamide HCl followed by $Na_2CO_3$ solution. Filter the reaction mixture on a 27 cm diameter porcelain Buchner funnel. Wash the off-white cake with (4×2000 g) potable water and then with (2×1578 g, 2000 mL) ethanol. Dam the cake on the Buchner funnel until dripping stops and then dry in a vacuum oven at 50° C. for 20 h.

| | |
|---|---|
| Yield | 83.4% |
| Total Imp (HPLC) | 0.96% |
| Sgl Imp (HPLC) | 0.3% |
| Ethanol (GC) | LT 0.01% |
| Water (KF) | 0.78% |

EXAMPLE 2

Preparation of N,N'-Bisacetamido-3-nitrobenzenesulfonamide

Charge N-acetamido-3-nitrobenzenesulfonamide (900 g, 3.47 mol) and N,N-dimethyl-formamide (6040 g, 6400 mL) to a 4-necked 12 L round-bottomed flask equipped with a mechanical stirrer, a temperature probe, a dropping funnel, a condenser and $N_2$ protection. Stir the resulting suspension at 20–25° C. until a complete solution forms. Add milled potassium carbonate (960 g, 6.95 mol) at 20–25° C. and heat the suspension to 50° C. Stir the reaction at this temperature for 0.5 hours. Cool the reaction mixture to 20–25° C. and then add a solution of the 2-chloroacetamide (487 g, 5.21 mol) in DMF (2450 g, 2600 mL) at a rate that maintains a pot temperature of 22–25° C. Use DMF (95 g, 100 mL) as a rinse. Stir the mixture at 22–25° C. for 15 minutes. Heat the reaction mixture to 50° C. over a 1 hour period and stir for 18 hours. Cool the reaction to 20–25° C. over a 0.5 hour period. Add water (9000 g) from a dropping funnel over 1 hour, using ice/water cooling to maintain a pot temperature of 20–25° C. Once addition is complete stir the suspension at 20–25° C. for 0.5 hour. Filter the slurry on a 30 cm diameter porcelain Buchner funnel and rinse the cake with potable water (3×900 g). Dam the cake until dripping stops. Transfer the wet cake to a 12-L 4-necked round-bottomed flask equipped with a mechanical stirrer, a temperature probe, and $N_2$ protection. Add water (6000 g) to the solid and stir the resulting slurry at 20–25° C. for 0.5 hour. Filter the cake on a (24 cm diameter) porcelain Buchner funnel. Wash the cake with potable water (3×900 g) and then with acetone (2×710 g, 2×900 mL). Dam the cake for 0.5 hour. Dry the solids in a vacuum oven at 50° C. for 20 hours.

| | |
|---|---|
| Yield: | 97.2% |
| Total Imp. (HPLC) | 1.10% |
| Largest Single Imp. (HPLC) | 0.56% |
| Acetone (GC) | LT 0.03% |
| DMF (GC) | LT 0.07% |
| Water (KF) | 0.29% |

EXAMPLE 3

Preparation of N,N'-Bisacetamido-3-aminobenzenesulfonamide

Charge a 2 gallon hydrogenation reactor with N,N'-bisacetamido-3-nitrobenzene-sulfonamide (800 g, 2.53 mol), wet 10% Pd/C (80 g), and N,N-dimethylformamide (3020 g, 3200 mL). Hydrogenate at 20–25° C. (25 psi) until hydrogen uptake has ceased. Expect 1.5–2.5 hours for completion. Check for reaction completion by HPLC. Filter the reaction through a cartridge filter into a 22 L three-necked round-bottomed flask fitted with a mechanical stirrer. Use N,N-dimethylformamide (2×400 mL, 755 g total) as a rinse. While stirring rapidly add water (8000 g) in a stream over about 0.45 hour, maintaining the pot temperature at 20–30° C. Hold the slurry at 20–25° C. for about 0.5 hour. Cool to 0–5° C. over a 0.5 hour period and hold for 1 hour. Filter the cake on a porcelain Buchner funnel. Wash the cake with water (3×800 g) previously cooled to 0–5° C. Dam the cake until dripping stops. Dry at 55° C. under vacuum for 40 hours.

| | |
|---|---|
| Yield: | 80% |
| Total Imp. (HPLC) | 0.68% |
| Largest Single Imp. (HPLC) | 0.48% |
| DMF (GC) | 0.06% |
| Water (KF) | 0.04% |

EXAMPLE 4

Preparation of Chlorodi(bis-acetamidoaminobenzenesulfonamide)triazine

Charge a 5-L 3-necked round-bottomed flask equipped with a mechanical stirrer, a temperature probe, a dropping funnel, a condenser and N₂ protection. with N,N'-bisacetamido-3-aminobenzenesulfonamide (500 g) and 1-methyl-2-pyrrolidinone (2270 g, 2200 mL), and stir at 20–25° C. for approximately 20 minutes. Add sodium carbonate (185 g) and cool the slurry to a temperature of from about −10 to 0° C. Add cyanuric chloride (169 g) in at least 6 equal portions over approximately 1.5 hours while not allowing the internal temperature to exceed about −5 to 0° C. Adjust the pot temperature to 0–5° C. and hold for about 3 hours. Warm to about 20–25° C. over a 3 hour period and hold for about 15 hours. Check for completion by HPLC. Add Celite (100 g) to the batch and stir for about 5 minutes. Filter the slurry onto a 21 cm Buchner funnel containing a pad of celite. Use 1-methyl-2-pyrrolidinone (2×517 g, 2×500 mL) as a rinse. Dam the cake until dripping stops. Charge a 12-L 3-necked round-bottomed flask equipped with a mechanical stirrer, a temperature probe, a dropping funnel, a condenser and N₂ protection with acetonitrile (3930 g, 5000 mL). While stirring add the filtrate to the stirring acetonitrile over a 0.5 h period. Hold the slurry at 20–25° C. for 2 h. Filter the slurry on a 26.5 cm diameter porcelain Buchner funnel and rinse the cake with acetonitrile (3×393 g, 3×500 mL). Dam the cake until dripping stops. Charge a 12-L 3-necked round-bottomed flask equipped with a mechanical stirrer, a temperature probe, a condenser and N₂ protection with 1-methyl-2-pyrrolidinone (3100 g, 3000 mL) and the wet cake. While stirring heat the mixture to about 80° C. A milky solution forms. Add acetonitrile (2360 g, 3000 mL) over a 20 minute period while maintaining the pot temperature at 75–80° C. Cool the solution to 20–25° C. over a 2 hour period and hold at 20–25° C. for approximately 1 hour. Filter the slurry on a 32.5 cm diameter porcelain Buchner funnel and rinse the cake with acetonitrile (3×310 g, 3×300 mL). Dam the cake until dripping stops. Dry at a temperature of from about 65–70° C. under high vacuum for 24 hours. The resulting product can be further purified by recrystallization from 1-methyl-2-pyrrolidinone-water mixture.

funnel containing a pad of celite. Use methanol-dimethyl sulfoxide (1:1 v/v) (2×397 g, 2×420 mL) as a rinse. Charge a 12-L 3-necked round-bottomed flask equipped with a mechanical stirrer, a temperature probe, a dropping funnel, a condenser and N₂ protection with previously filtered methanol (4049 g, 5112 mL). Add the filtrate from step 5 slowly over a 45 min period and continue stirring for 0.5 h. Under nitrogen filter the slurry onto a 32 cm Buchner funnel containing a polypropylene pad. Rinse the cake with previously filtered methanol-dimethyl sulfoxide (4:1 v/v) (2×399 g, 2×390 mL), followed by methanol (309 g, 390 mL). Dam the cake until dripping stops. Charge a 5-L 3-necked round-bottomed flask equipped with a mechanical stirrer and N₂ protection with the wet cake from step 9 and methanol (1869 g, 2360 mL). Stir the slurry for about 1 hour. Filter the slurry onto a 32 cm Buchner funnel containing a polypropylene pad. Rinse the cake with previously filtered methanol (2×309 g, 2×390 mL). Dam the cake until dripping stops. Dry the solid at 58–62° C. under high vacuum for 30 hours. The solid weighs (241 g). Charge a 6-L 3-necked round-bottomed flask equipped with a mechanical stirrer, a temperature probe, a condenser and N₂ protection with the solid, previously filtered purified water (6 times the weight of solid, 1440 g) and previously filtered acetonitrile (566 g, 719 mL, 2.36 times the weight of solid). While stirring heat the mixture to 65–70° C. A solution forms. The pH is 7–7.5. Add previously filtered acetonitrile (1770 g, 2249 mL, 7.06 times the weight of solid) over a 20 min period while maintaining the pot temperature at 65–70° C. Seed the stirring solution with product and cool to 49–51° C. over a 0.5 h period. Hold at 49–51° C.) for 2 hours. Under nitrogen filter the hot slurry on a 25 cm diameter porcelain Buchner funnel and rinse the cake with previously filtered acetonitrile-water (2:1 v/v) (3×172 g, 3×200 mL) at 48–52° C. Dam the cake until dripping stops after each wash. Dry the product at 60–65° C., 5 mm Hg for 24 h.

| | |
|---|---|
| Yield | 81% |
| Total Imp (HPLC) | 0.89% |
| Largest Single Imp (HPLC) | 0.19% |
| 1-Methyl-2-pyrrolidone (GC) | 11.3% |
| Acetonitrile (GC) | LT 0.01% |
| Water (KF) | 0.49% |

EXAMPLE 5

Preparation of 4,4'-Bis-{4,6-bis-[3-(bis-carbamoylmethyl-sulfamoyl)-phenylamino]-[1,3,5]triazin-2-ylamino}-biphenyl-2,2'-disulfonic Acid, Disodium Salt Charge a 5-L 3-necked round-bottomed flask equipped with a mechanical stirrer, a temperature probe, a dropping funnel, a condenser and N₂ protection with chlorodi-(bis-acetamidoaminobenzenesulfonamide)triazine, (393 g), 4,4'-diamino-2,2'-biphenyl-disulfonic acid, disodium salt (85.1 g), N,N-diisopropylethylamine (62.4 g, 84.0 mL) and dimethyl sulfoxide (1412 g, 1284 mL). While stirring heat the mixture to 68–72° C. Stir the mixture at 68–72° C. for about 96 hours. Check for reaction completion by HPLC. Adjust the pot temperature to 20–25° C. and add slowly methanol (1017 g, 1284 mL) followed by celite (100 g). Stir the mixture for 15 min and then filter the slurry onto a Buchner

| | |
|---|---|
| Yield: | 37% |
| Total Imp (HPLC) | 2.49% |
| Sgl Largest Imp (HPLC) | 0.50% |
| DMSO (GC) | 0.13% |
| Acetonitrile (GC) | 0.31% |
| Methanol (GC) | 0.01% |
| Water (KF) | 2.58% |
| Water (GC) | 1.10% |
| Sodium | 2.35% |

What is claimed is:

1. A method for preparation of 2-[Carbamoylmethyl-(3-nitro-benzenesulfonyl)-amino]acetamide, the method comprising reacting 2-(3-Nitro-benzenesulfonylamino)acetamide with N,N-Dimethylformamide in the presence of ClCH₂CONH₂ and a base.

2. The method of claim 1 wherein the base is sodium carbonate, potassium carbonate or sodium bicarbonate.

3. The method of claim 1 further comprising an initial step of preparing 2-(3-Nitro-benzenesulfonylamino)-acetamide by reacting 3-Nitro-benzenesulfonyl chloride with aminoglycine hydrochloride or its free base in a basic reaction medium.

4. A compound, 2-(3-Nitro-benzenesulfonylamino)-acetamide.

* * * * *